(12) United States Patent
Kato et al.

(10) Patent No.: US 7,117,703 B2
(45) Date of Patent: Oct. 10, 2006

(54) WIRE-STRANDED HOLLOW COIL BODY, A MEDICAL EQUIPMENT MADE THEREFROM AND A METHOD OF MAKING THE SAME

(75) Inventors: Tomihisa Kato, Nagoya (JP); Kenji Miyata, Nagoya (JP)

(73) Assignee: Asahi Intecc Co., Ltd., Aichi-ken (JP)

( * ) Notice: Subject to any disclaimer, the term of this patent is extended or adjusted under 35 U.S.C. 154(b) by 0 days.

(21) Appl. No.: 10/611,664

(22) Filed: Jul. 2, 2003

(65) Prior Publication Data
US 2004/0116833 A1 Jun. 17, 2004

(30) Foreign Application Priority Data
Dec. 11, 2002 (JP) ............................. 2002-358851

(51) Int. Cl.
*B21F 3/02* (2006.01)

(52) U.S. Cl. ............................... 72/135; 140/4; 140/34; 140/71 C; 138/23; 138/130; 138/134; 72/146; 72/371; 600/139

(58) Field of Classification Search ................ 600/139
See application file for complete search history.

(56) References Cited

U.S. PATENT DOCUMENTS

| | | | | |
|---|---|---|---|---|
| 4,932,419 A | * | 6/1990 | de Toledo | 600/585 |
| 5,373,619 A | * | 12/1994 | Fleischhacker et al. | 29/451 |
| 5,376,083 A | * | 12/1994 | Mische | 604/264 |
| 5,840,046 A | * | 11/1998 | Deem | 600/585 |
| 5,932,035 A | * | 8/1999 | Koger et al. | 148/563 |
| 5,984,877 A | * | 11/1999 | Fleischhacker, Jr. | 600/585 |
| 6,436,056 B1 | * | 8/2002 | Wang et al. | 600/585 |
| 6,589,227 B1 | * | 7/2003 | Sønderskov Klint | 604/524 |
| 2003/0069522 A1 | * | 4/2003 | Jacobsen et al. | 600/585 |

FOREIGN PATENT DOCUMENTS

| | | |
|---|---|---|
| JP | 4-309371 | 10/1992 |
| JP | 7-213481 | 8/1995 |
| JP | 10-165361 | 6/1998 |
| JP | 10-290803 | 11/1998 |
| JP | 11-025758 | 1/1999 |
| JP | 11-033004 | 2/1999 |
| JP | 11-104071 | 4/1999 |
| JP | 2000-512691 | 9/2000 |
| JP | 2002-275774 | 9/2002 |
| WO | 98/46804 | 10/1998 |

* cited by examiner

*Primary Examiner*—Beverly M. Flanagan
*Assistant Examiner*—Matthew J. Kasztejna
(74) *Attorney, Agent, or Firm*—Morgan, Lewis & Bockius, LLP

(57) ABSTRACT

A wire-stranded hollow coil body (1) has a multitude of coil line elements (2) stranded along a predetermined circular line to form a flexible wire tube having a central axial hollow portion (3), the flexible wire tube is stranded under a strand-turn resistant load and heat treated to remove a residual stress upon formation so as to provide a high rotation-following capability and a high straightness. Further, a method provides a way to strand the coil line elements (2) under a strand-turn resistant load while heat treating the coil line elements (2).

3 Claims, 11 Drawing Sheets

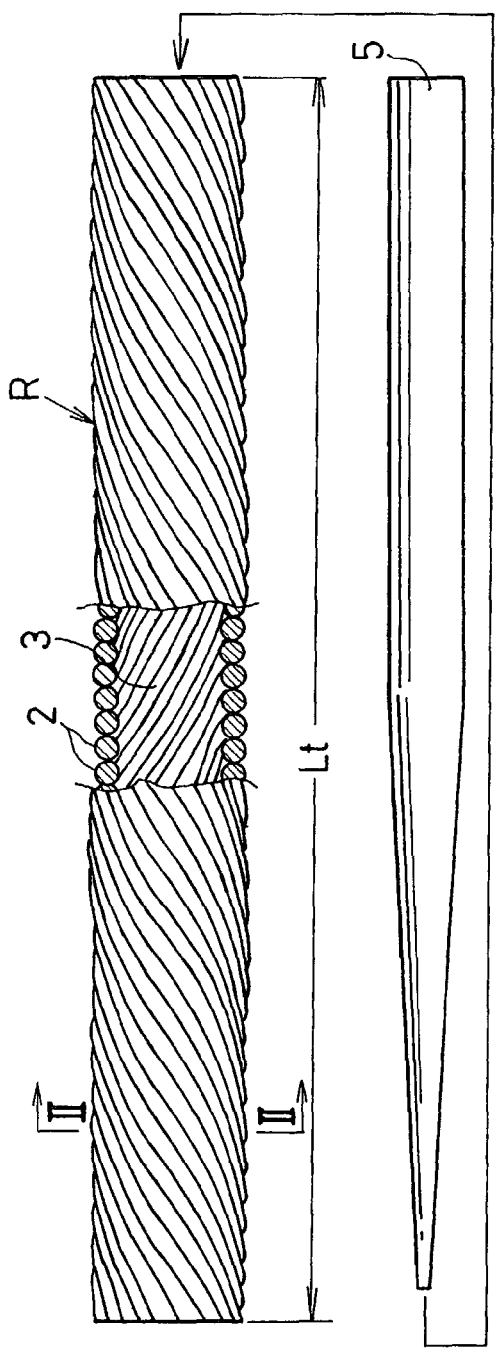
Fig1
Fig2
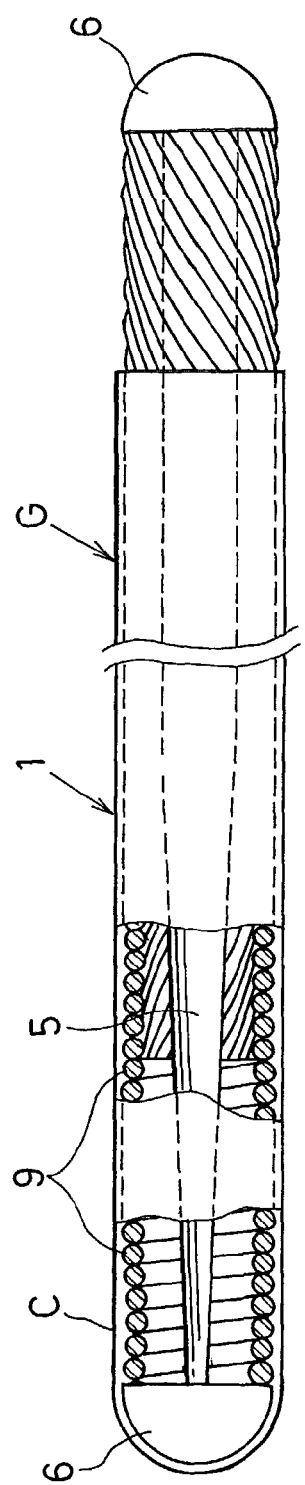
Fig3

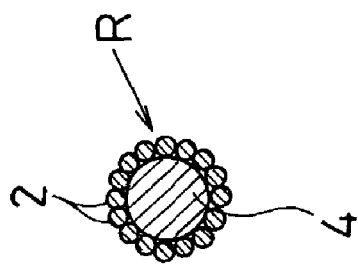
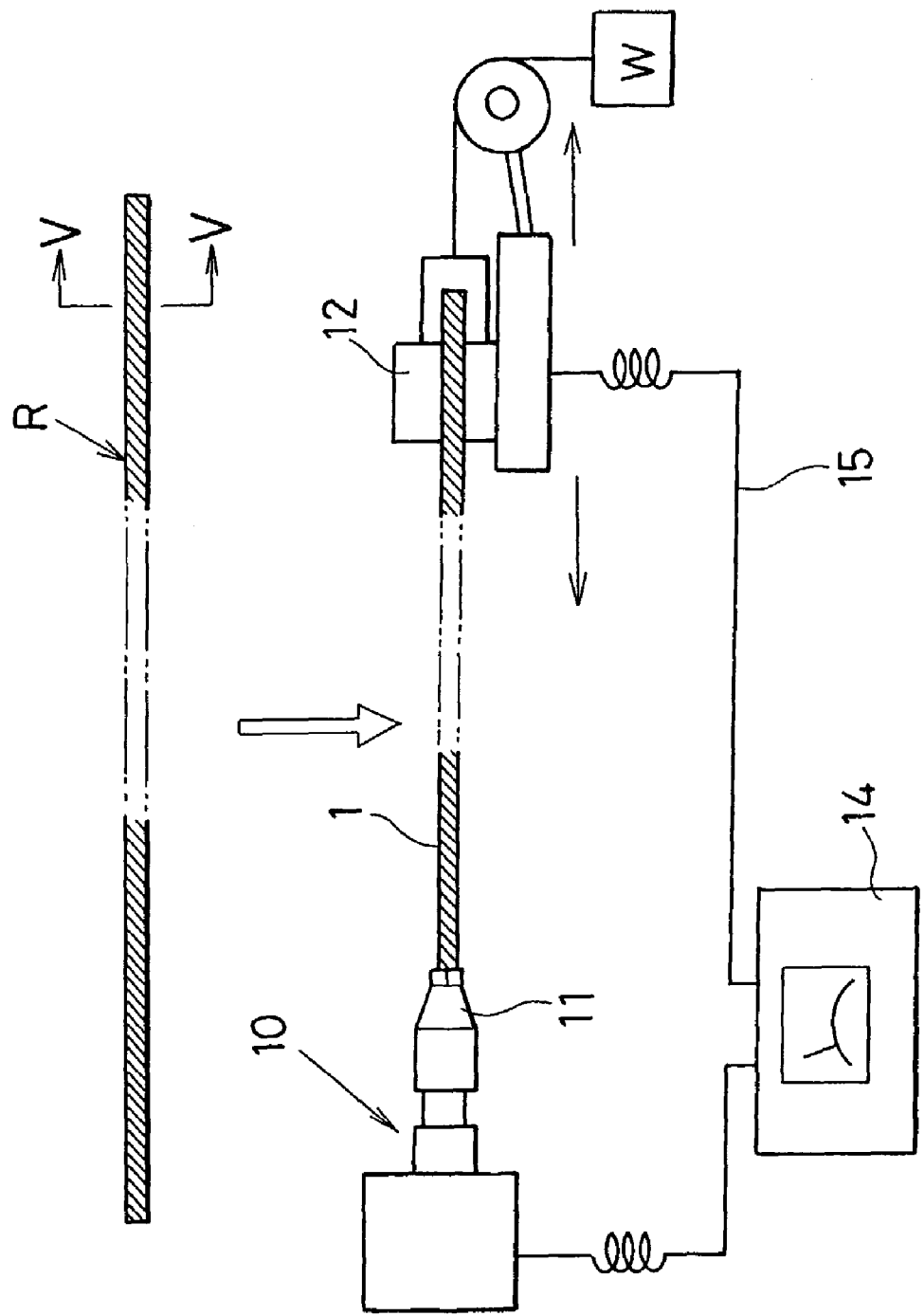

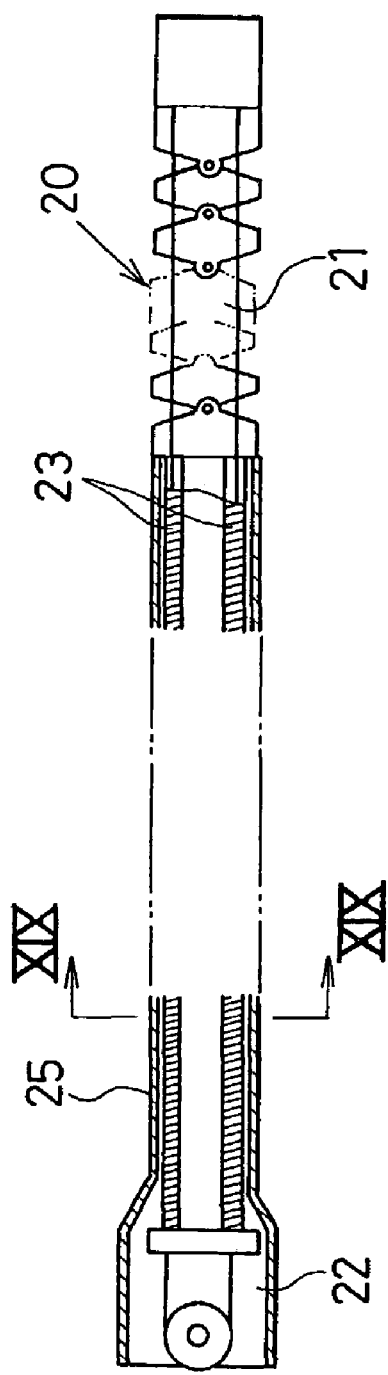
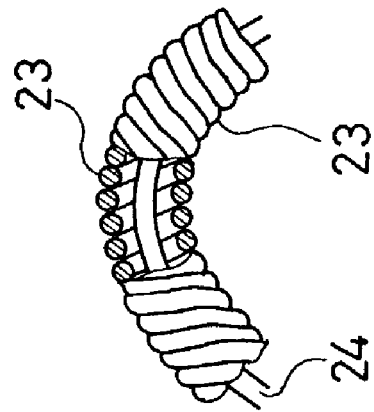
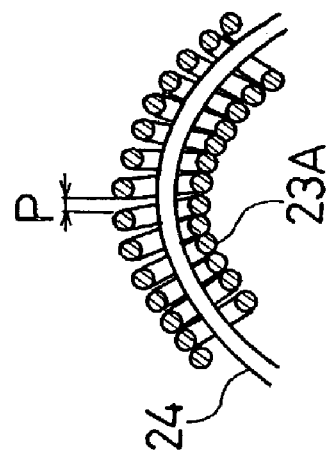
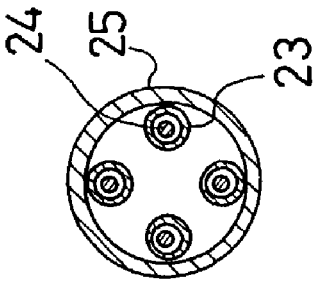
Related Art

WIRE-STRANDED HOLLOW COIL BODY, A MEDICAL EQUIPMENT MADE THEREFROM AND A METHOD OF MAKING THE SAME

BACKGROUND OF THE INVENTION

1. Field of the Invention

The invention relates to a wire-stranded hollow coil body used as a main wire component of a medical equipment in the form of flexible line wire such as a catheter, catheter guide wire, endscope treating tool or the like, and more particularly concerns to a medical equipment produced therefrom and a method of making the wire-stranded hollow coil body.

2. Description of Related Art

In a catheter and a catheter guide wire which introduce a leading distal end into a diseased area through a twisted and turned vascular system, a leading distal end of the catheter or the catheter guide wire is inserted into the blood vessel or the somatic cavity by a "push-pull and turn" manipulation at a hand access portion located ouside a subject patient upon treating the diseased area. In an endscope treating tool which is inserted through a somatic cavity to reach the diseased area, a leading end of the endscope treating tool is manipulated in the same manner as mentioned above.

In order to achieve a smooth manipulation when inserting the leading distal end into the somatic cavity and the blood vessel, it is required for these medical devices to have multi-mechanical properties. The multi-mechanical properties includes a high flexibility, a good straightness in free state and a good restitutivity against bending deformation. The medical devices of this type are required at its leading distal end portion to have a high flexibility, while at the same time, having at its rear portion to have an appropriate rigidity as a functionally gradient property. It is also indispensable for the leading distal end to have a high maneuverability in which the leading distal end properly responds to the hand operation which is to be done outside the subject patient.

The following related art flexible linear wires used as a main component of the medical devices have been produced to achieve the above indispensable multi-mechanical properties.

In the references of Laid-open Japanese Patent Application Nos. 2002-275774 and 4-309371 (referred in turn to as "first and second reference" hereinafter), a wire-stranded hollow coil body is disclosed which have a multitude of coil line elements stranded along a predetermined circular line to form a rope-like flexible linear tube having a central axial hollow portion. In the domestic publication of Japanese Patent Application No. 2000-512691 (referred to as "third reference" hereinafter), a solid thin wire made from an elastic shape-memory alloy is stranded under a tensile load. The solid thin wire thus stranded is subjected to a stress-removing heat-treatment procedure under the condition of approx. 280° C.×30 min. −300° C.×30 min. so as to provide a flexible solid wire body used for medical devices.

The reference of Laid-open Japanese Patent Application No. 10-165361 (referred to as "fourth reference" hereinafter) discloses a helical hollow pipe to produce a sheath from an elongated hollow thin wire used for an endscope treating tool. An outer surface of the helical hollow pipe is partly ground to form a diameter-reduced portion, or partly replaced by a thin wire to provide a good bending capability with the sheath.

The reference of Laid-open Japanese Patent Application No. 11-104071 (referred to as "fifth reference" hereinafter) discloses a flexible wire sheath made from a multi-wound helical coil body used for an endscope treating tool. Into the flexible wire sheath, a manipulation wire is inserted so as to be rotatable with a biopsy end portion in unison.

The reference of Laid-open Japanese Patent Application No. 11-33004 (referred to as "sixth reference" hereinafter) discloses a pressure-sensor type guide wire in which a guide wire sensor portion is made from a stainless steel cloak tube having a platinum helical wire tube and a stainless steel helical wire tube concentrically placed to enclose a piezo-electric elongation plate. The reference of Laid-open Japanese Patent Application No. 7-213481 (referred to as "seventh reference" hereinafter) discloses a flexible endscope in which a manipulation wire is placed within a cloak tube having four flexible helical wires juxtaposed,each of which is wound to have a different helical pitch. The reference of Laid-open Japanese Patent Application No. 10-290803 (referred to as "eighth reference" hereinafter) discloses an endscope treating tool in which a flexible wire coil sheath constitutes a main structure.

In the catheter, the catheter guide wire and the endscope tube made from the wire-stranded hollow coil body disclosed by the first and second references, the wire-stranded hollow structure makes it possible to present a good flexibility based on the wire-stranded body construction per se. The wire-stranded hollow structure advantageously reduces a torsion-resistant moment upon manipulation, while at the same time, reducing a weight dimension per unit length. However, in contrast to the above advantages, the preceding references has the following drawbacks.

Namely, both the references lack a lengthwise linearity and a rotation-following capability responsive to the manipulation of the leading distal end, and have no gradient flexibility in which the wire-stranded body gradually shifts its property in the lengthwise direction while substantially maintaining uniform torsion-resistant and flexible properties among the multi-mechanical properties. The flexible solid wire body disclosed by the third reference is made from the solid thin wire deviod of the central hollow portion, this increases a torsional resistance, and adding the weight dimension per unit length too much to put the flexible solid wire body into practical use for the medical devices.

The wire-stranded hollow coil structure disclosed by the fourth to sixth references is unsatisfactory from the point of the indispensable requirement to function as a main linear body for the medical devices because both the references lack the lengthwise linearity and the rotation-following capability while maintaining the uniform torsion-resistant property and flexible property, as is the case with the first and second references.

Therefore, it is an object of the invention to overcome the above drawbacks so as to provide a wire-stranded hollow body, a medical equipment formed therefrom and a method of making the same in which the medical equipment having the flexible line wire as a main wire component is remarkably improved at its performance.

SUMMARY OF THE INVENTION

According to the present invention, there is provided a wire-stranded hollow coil body including a multitude of coil line elements stranded along a predetermined circular line to form a flexible linear tube having a central axial hollow portion, whereby the flexible linear tube is stranded under a strand-turn resistant load and heat treated to remove a residual stress upon formation so as to provide a high rotation-following capability and a high straightness. Medical equipments such as a medical endscope, an endscope treating tool and a pressure sensor type medical guide wire are constructed with the wire-stranded hollow coil body a main wire component.

According to other aspect of the present invention, there is provided a method of making the wire-stranded hollow coil body including a multitude of coil line elements stranded along a predetermined circular line to form a flexible linear tube having an axial hollow portion, the method having steps of clamping one end of a primary forming flexible linear tube by means of a rotationally active chuck, and arranging the other end of the primary forming flexible linear tube to be slidable in its lengthwise direction, and clamping the other end by a fixture chuck to impart a tensile force with the primary forming flexible linear tube; actuating the rotationally active chuck to strand the primary forming flexible linear tube, and concurrently or thereafter heat treating the primary forming flexible linear tube to remove a residual stress upon forming the coil line elements by electrically conducting between the rotationally active chuck and the fixture chuck.

According to other aspect of the present invention, there is provided a method of making the wire-stranded hollow coil body including a multitude of coil line elements stranded along a predetermined circular line to form a flexible linear tube having a central axial hollow portion, the method having steps of clamping one end of a primary forming flexible linear tube by means of a rotationally active chuck, and clamping halfway middle portions of the primary forming flexible linear tube by means of middle clamp portions, and stranding the primary forming flexible linear tube in different strand turns depending on spans between the rotationally active chuck and each of the middle clamp portions.

According to other aspect of the present invention, there is provided a method of making the wire-stranded hollow coil body including a multitude of coil line elements stranded along a predetermined circular line to form a flexible linear tube having a central axial hollow portion, the method having steps of concurrently or after stranding a primary forming flexible linear tube, accommodating lengthwisely divided sections of a primary forming flexible linear tube into heating devices, each of which has different heating conditions depending on the lengthwisely divided sections, so as to heat treat the pluralistically divided sections individually to have residual stresses removed in different degrees.

The wire-stranded hollow coil body is such that characteristics such as a high rotation-following capability and a high straightness are provided to produce a high quality wire-stranded structure in which a group of the coil line elements is stranded to form the flexible wire tube configuration. It is to be noted that the primary forming flexible linear tube may be represented by an ordinary wire rope configuration in which the group of the coil line elements is stranded around an outer surface of an elongated core line.

In order to further improve the performance depending on its application and usage, the wire-stranded hollow coil body constructed as follows:

The lengthwisely divided sections of the primary forming flexible linear tube are constructed to have different degree of stranding turns and the residual stresses removed in different degrees; the outer surface of the group of the stranded coil line elements is ground in a manner to be diametrically reduced in concentrical relationship with the wire-stranded hollow coil body; alternatively, the coil line elements are specified by an austenitic stainless steel; the outer surface of the flexible linear tube is electrolytically polished; the flexible linear tube is in some turns unwound reversely after stranded.

The wire-stranded hollow coil body is such that it is stranded under the torsion-resistant load (tensile load in the lengthwise direction), and heat treated to remove the residual stress so as to provide the high rotation-following capability and high straightness. A good manipulation response is obtained at the flexible hollow line wire of the medical equipment upon push-pull manipulating the hand access portion to insert the leading distal end portion into the vascular system or the somatic cavity for an appropriate treatment. The structure enables a manipulator to a good straightness felt before and after inserting into the vascular system or the somatic cavity, and representing a lightweight structure due to the wire-stranded hollow configuration while ensuring a high twisting capability due to a reduced bending rigidity to produce a high quality line wire tube.

Upon stranding the group of the coil line elements, the flexible linear tube generally generates rolls or swells transmitting in the lengthwise direction due to a contractile stress produced between the neighboring coil line elements tightly arranged and due to a tensile and shearing stress appeared between the coil line elements. In contrast to the above situation, the hollow wire coil configuration according to the invention is stranded under the torsion-resistant load, and heat treated to remove the residual stress. This obviates a chance to occur the detrimental roll or swell phenomenon produced due to the complicated stresses combined, thus providing the wire-stranded hollow configuration with a good straightness. This also achieves a good rotation-following capability in which the leading distal end staunchly follows the rotational manipulation of the hand access portion. The related art wire-stranded hollow coil body disclosed by the first and second references intermittently generates "strand stuck portions", a part of which is rapidly released with an excessive times of turning operation so as to roll in the stick slip manner. This produces a zigzag curve represented by broken lines in FIG. 31 which indicates that the rotational manipulation of the hand access portion at an angle ($\theta 2$) results in twisting the leading distal end by an angle ($\theta 1$). On the contrary, the wire-stranded hollow coil body according to the invention is stranded under the torsion-resistant load to eliminate the unfavorable "strand stuck portions" so as to present the high rotation-following capability and high straightness as shown by a linear relationship represented by the solid line in FIG. 31.

The wire-stranded hollow coil body according to the invention serves as a main wire component of a high quality medical device in which the wire-stranded hollow coil body is equipped with a high rotation-following capability and a high straightness.

With the former method of making the wire-stranded hollow coil body, it is possible to mass produce the wire-stranded hollow coil body efficiently with a relatively low cost. With the latter method of making the wire-stranded hollow coil body, it is possible to produce the lengthwisely divided sections of the primary forming flexible linear tube to have different strand turns and residual stresses removed in different degrees. This leads to efficiently mass producing the fuctionally gradient type wire-stranded hollow coil body which has a high flexibility at the leading distal end portion, a moderate flexibility at the halfway middle portion and a high rigidity at the rear end portion.

BRIEF DESCRIPTION OF THE DRAWINGS

A preferred form of the present invention is illustrated in the accompanying drawings in which:

FIG. 1 is an exploded plan view of a wire-stranded hollow coil body according to a first embodiment of the invention;

FIG. 2 is a latitudinal cross sectional view taken along the line II—II of FIG. 1;

FIG. 3 is a plan view of a medical guide wire into which the wire-stranded hollow coil body is incorporated but partly sectioned;

FIG. 4 is an explanatory view showing how the wire-stranded hollow coil body is manufactured;

FIG. 5 is a latitudinal cross sectional view taken along the line V—V of FIG. 4;

FIG. 18 is a plan view of a flexible endscope;

FIG. 19 is a latitudinal cross sectional view taken along the line XIX—XIX of FIG. 18;

FIG. 20 is an explanatory view of a related art flexible endscope shown for comparison;

FIG. 21 is an explanatory view of the flexible endscope;

DETAILED DESCRIPTION OF THE PREFERRED EMBODIMENTS

Figure 6:
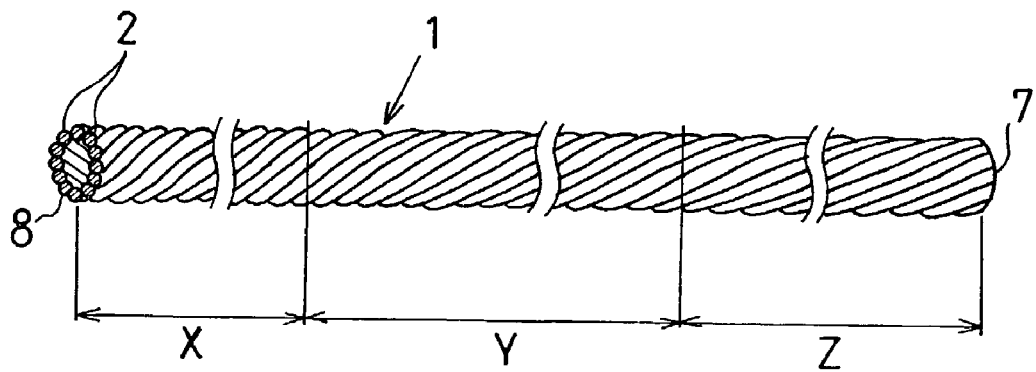
FIG. 6 is a plan view of a wire-stranded hollow coil body according to a second embodiment of the invention.

Referring to FIGS. 1 through 5, with the use of a first method of making a wire-stranded hollow coil body 1, the wire-stranded hollow coil body 1 according to a first embodiment of the invention is described. In order to use an enlongated thin flexible wire to a medical guide wire, a multitude of austenitic stainless steel coil line elements 2 are stranded along a predetermined circular line to form a flexible linear metallic tube, a space of which serves as a central axial hollow portion 3. An entire length (Lt) of the flexible linear tube measures approx. 1.000 –1.500 mm.

The group of the coil line elements 2 is stranded under a strand-turn resistant load (torsion-resistant load) and heat treated to remove a residual stress appeared during the stranding and drawing operation. The wire-stranded hollow coil body 1 thus formed is provided with a high straightness having a straight configuration in free state devoid of the unfavorable roll or swell phenomenon. The wire-stranded hollow coil body 1 is further provided with a high rotation-following capability in which the rotation of the thin flexible wire at one end is soomthly and efficiently transmitted to the other end of the thin flexible wire when one end of the thin flexible wire is rotated around the axial hollow portion 3.

The wire-stranded hollow coil body 1 is formed in accordance with the following first method (see FIG. 4). Namely, with the use of an ordinary wire rope stranding machine, a primary forming flexible linear metallic tube R (referred simply to as "primary approximation R") is formed as a normal wire rope structure having a predetermined length. One end of the primary approximation R is set at a rotationally active chuck 11 of a stranding machine 10. The other end of the primary approximation R is arranged to be slidable along its lengthwise direction, and clamped by a slide type fixture chuck 12 loaded with a static weight W. The torsion-resistant load under the tensile stress W is added to the primary approximation R set between the rotationally active chuck 11 and the slide type fixture chuck 12. Then, a conductor line 15 extended from an electric power generator 14 is connected between the rotationally active chuck 11 and the slide type fixture chuck 12, so as to apply an electric current to the primary approximation R to prepare for heat treatment of the primary approximation R.

The primary approximation R set under the torsion-resistant load and the heat treatment is turned 300 times in the stranding direction and unwound 100 times in the reverse direction (stranded 200 (300–100) times resultantly) as shown at (A) in Table 2. At the time of stranding the primary approximation R or after stranded the primary approximation R, the primary approximation R is heat treated due to its own electric resistor energized. After heat treating the primary approximation R, an elongated core 4 is withdrawn from the primary approximation R to provide the axial hollow portion 3 in which the elongated core 4 is placed so as to produce the wire-stranded hollow coil body 1.

A stainless steel or nickel-titanium alloy core 5 are placed in the axial hollow portion 3 as a flexible wire component needed to form the guide wire. To a front distal end of the wire-stranded hollow coil body 1, a single wound helical coil 9 is connected which is made from a radiopaque material to implement the fluorography while ensuring a high flexibility at the leading distal end of the wire-stranded hollow coil body 1 so as to provide a guide wire body of excellent quality. To the front distal end of the guide wire body, the core 5 is thermally bonded by a solder mass to substantially shape a semi-spherical bulge portion 6. To a rear distal end of the guide wire body, the core 5 is thermally bonded by a plasma welding to substantially shape the same semi-spherical bulge portion 6. An outer surface of the guide wire body is ground by an electrolytic polishing (well-known means including whetstone grinding), the electrolytically polished surface is coated with a hydrophilic polymer film C applied thereon to provide a medical guide wire. By way of illustration, a dimensional design of the wire-stranded hollow coil body 1 are shown in Table 2.

TABLE 2

| | A | B |
|---|---|---|
| dimension | 18 coil line elements stranded (line diameter: 0.55 mm) entire length: 4.500 mm outer diameter of coil: 0.415 mm inner diameter of coil: 0.305 mm | 8 coil line elements stranded (line diameter: 0.22 mm) entire length: 4.500 mm outer diameter of coil: 0.865 mm inner diameter of coil: 0.425 mm |
| stranded times | stranded 300 times but unwound 100 times | stranded 350 times but unwound 120 times |
| resistance heating | 2.8 Amp × 60 sec heating temp.: approx. 400–500° C. | 6.0 Amp × 60 sec heating temp.: approx. 400–500° C. |
| static load weight | 3.6 kg | 13.6 kg |

It is to be noted that upon forming the wire-stranded hollow coil body 1, it is unwound in the direction opposite to that of stranding the primary approximation R, if necessary, as shown at the dimensional design in Table 2. This is to stabilize the entire configuration by absorbing the spring back accompanied with the stranding operation, and avoiding the detrimental roll or swell phenomenon caused by an uneven quality when excessively stranded.

The wire-stranded hollow coil body 1 is represented by the lightweight structure per a unit length and a smooth twisting manipulation based on the hollow wire tube configuration. In addition to the preceding main advantages, an advantage specific to the first method of making the wire-stranded hollow coil body 1 is obtained.

With the coil line elements 2 made from the austenitic stainless steel (having a high coefficient of thermal expansion) and its outer surface electrolytically polished, secondary advantages are ensured. Namely, it is possible to provide the primary approximation R with a good drawability and heat-releasable capability at the time of thermally bonding bulge portion 6, so as to alleviate the residual stress in the primary approximation R to help stabilize the main advantages. Due to the electrolytically polished surface, it is possible to ensure a smooth and erosion-resistant surface to stabilize an improved performance as a main wire component of the medical equipment.

Figure 7:
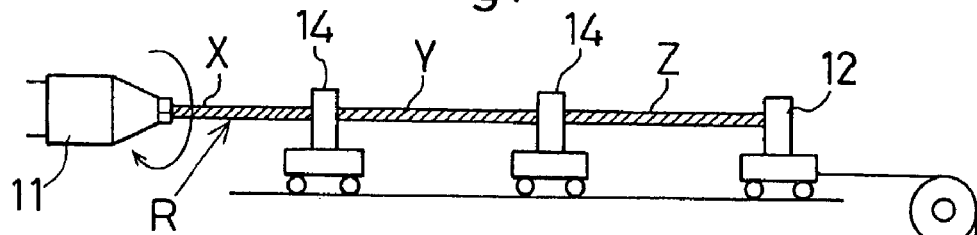
FIG. 7 is an explanatory view showing how the wire-stranded hollow coil body is manufactured.

Referring to FIGS. 6 through 17, a second embodiment of the invention is described in conjunction with a second and third method of making the wire-stranded hollow coil body 1. The primary approximation R, in which the coil line elements 2 are stranded along the predetermined circular line, is lengthwisely divided into three sections X, Y and Z, each of which has different number of strand turns as shown in FIGS. 6 and 7. When applied to the medical guide wire, the section X has maximum strand turns provided at a hand access portion 8, the section Z has a minimum strand turns provided at the leading distal end 7, and the section Y has a middle number of the strand turns provided at the halfway middle portion. The number of the strand turns progressively decreases from the section X through the section Y to the section Z, a helical pitch of which reversely increases respectively in the same order.

Figure 8:
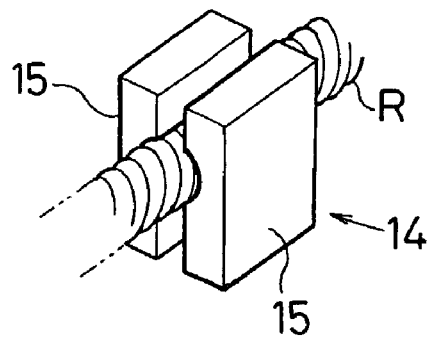
FIG. 8 is a perspective view of a clamp portion.

The wire-stranded hollow coil body 1 is placed between the rotationally active chuck 11 and the fixture chuck 12 of the stranding machine 10, and a slidable clamp portion 14 is placed at the boundary between the sections X, Y and Z to clamp each section by paired clamp plates 15, 15 as shown in FIG. 8. By clamping each of the sections, it is possible to produce the wire-stranded hollow coil body 1 of different strand turns depending on its sections X, Y and Z by way of the second method of making the wire-stranded hollow coil body 1.

Figure 9:
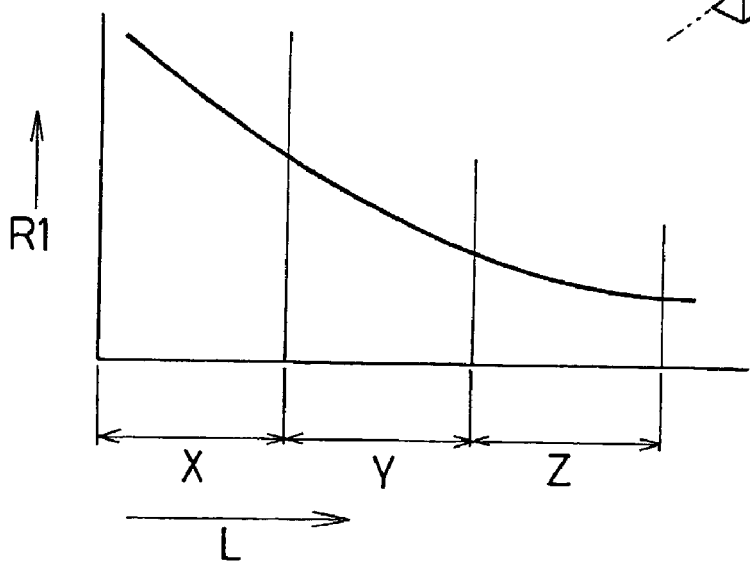
FIG. 9 is a characteristic curve of the wire-stranded hollow coil body.

Each of the sections X, Y and Z has the different strand turns and represents a bending characteristics depending on the strand turns provided among multi-mechanical properties. The hand access portion 8 has a maximum rigidity which is manipulated outside the patient's body as the flexible linear tube of the medical equipment. The leading distal end portion has a highly pliable and flexible property which is introduced into the vascular system and the somatic cavity. As shown in FIG. 9, the primary approximation R has a bending rigidity (R1) successively reducing along the length dimension (L) to produce a high quality flexible linear tube as a functionally gradient substance which gradually shifts the property from a highly rigid section to a flexible section.

Figure 10:
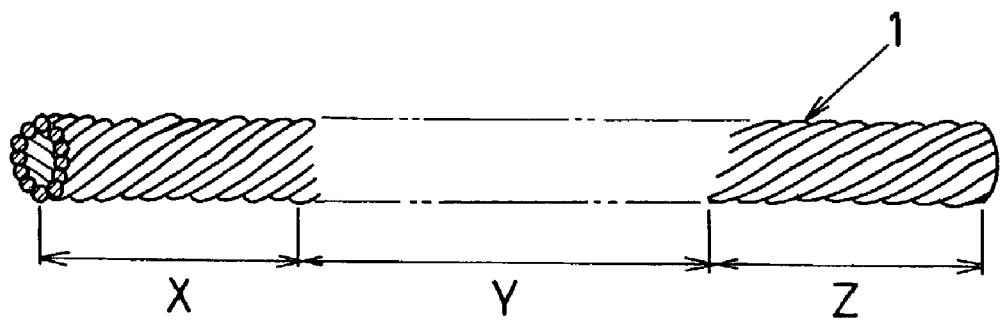
FIG. 10 is a wire-stranded hollow coil body according to a third embodiment of the invention.
Figure 11:
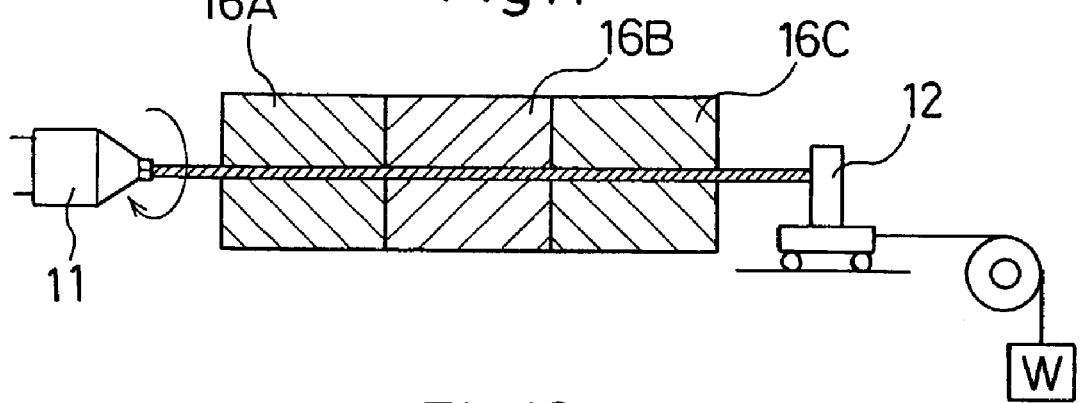
FIG. 11 is an explanatory view showing how the wire-stranded hollow coil body is manufactured.
Figure 12:
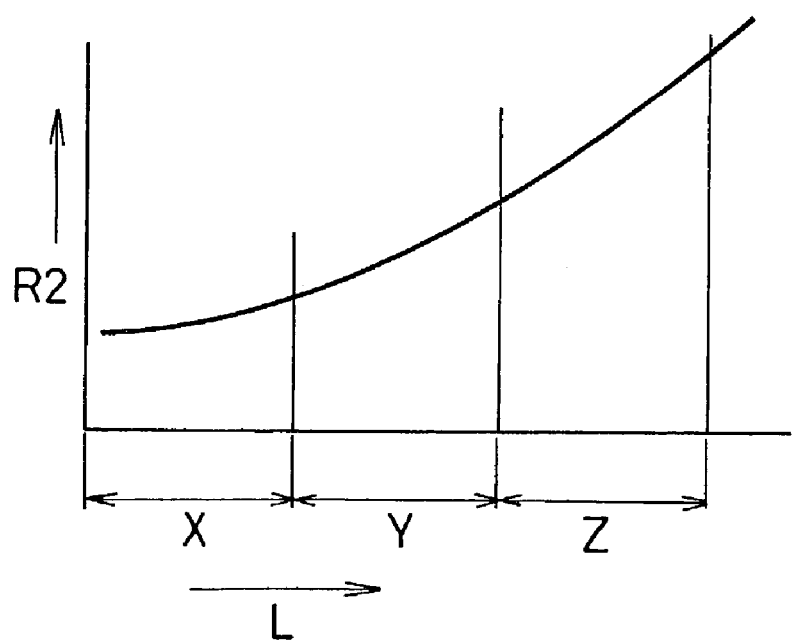
FIG. 12 is a characteristic curve of the wire-stranded hollow coil body.
Figure 15:
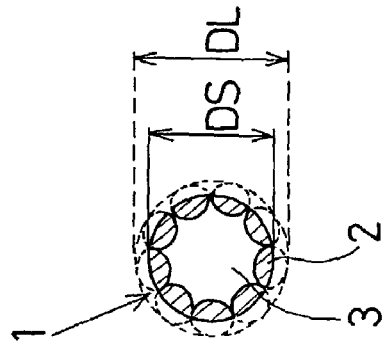
FIG. 15 is a latitudinal cross sectional view taken along the line XV—XV of FIG. 16.
Figure 14:
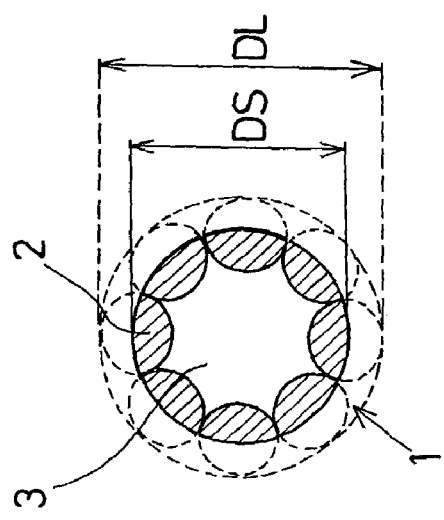
FIG. 14 is a latitudinal cross sectional view taken along the line XIV—XIV of FIG. 16.
Figure 13:
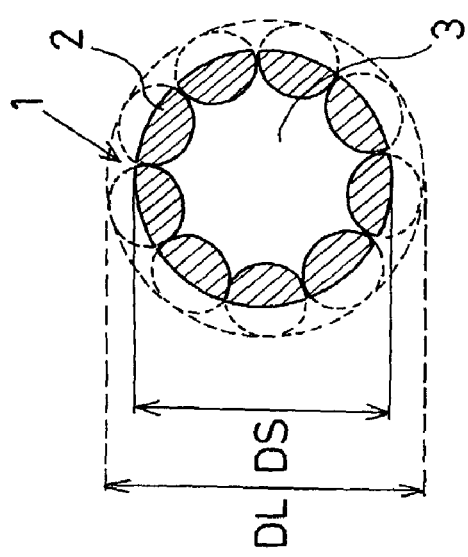
FIG. 13 is a latitudinal cross sectional view taken along the line XIII—XIII of FIG. 16 according to a fourth embodiment of the invention.
Figure 16:
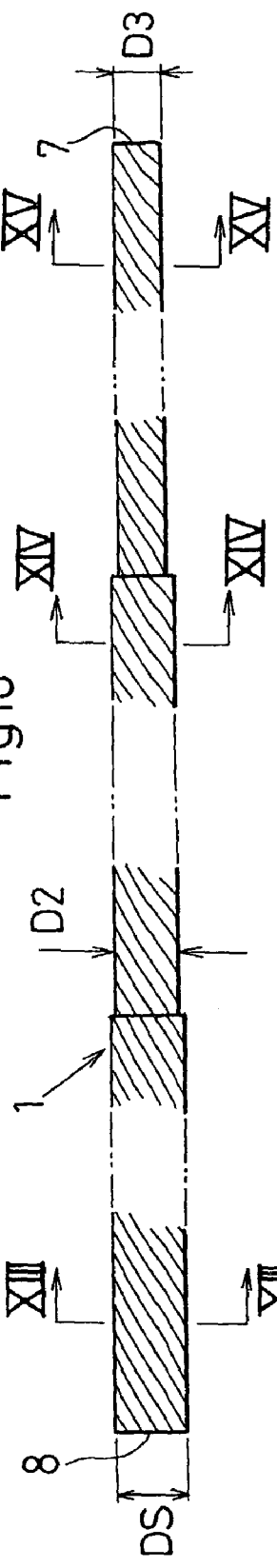
FIG. 16 is a plan view of a wire-stranded hollow coil body.
Figure 17:
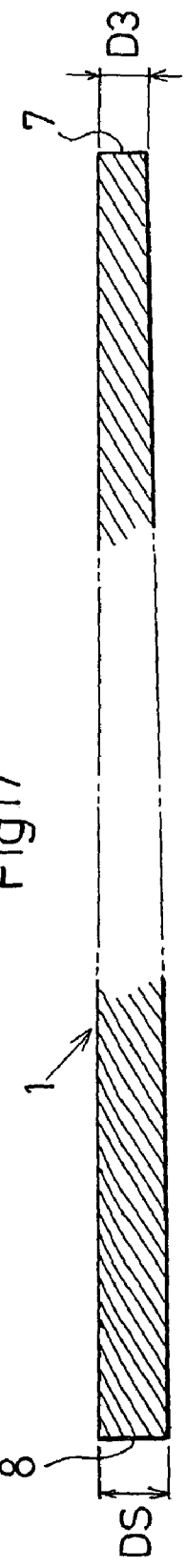
FIG. 17 is a plan view of a modified wire-stranded hollow coil body.

FIGS. 10 through 12 show a third embodiment of the invention in which the individually divided sections X, Y and Z are placed respectively at three heating devices 16A, 16B and 16C each having different heating condition. The primary approximation R is heat treated by energizing the devices 16A, 16B and 16C concurrently at the time of stranding the primary approximation R or after the primary approximation R is stranded, so as to remove the residual stress upon formation by a third method of making the wire-stranded hollow coil body 1. Depending on the heating condition of the heating devices 16A, 16B and 16C, the sections X, Y and Z are heat treated differently to have the residual stresses removed in different degrees. This provides the wire-stranded hollow coil body 1 with the functionally gradient "tensile strength" and "bending rigidity (R2)" each gradually shifting in the lengthwise direction (L) so as to produce a high quality flexible linear tube as shown in FIG. 12.

FIGS. 13 through 17 show a fourth embodiment of the invention in which an outer surface of the group of the coil line elements 2 is ground in concentric relationship with the central axial hollow portion 3 to reduce an original outer diameter (DL) into a reduced outer diameter (DS). As shown at diametrical dimensions DS, D2 and D3 in FIG. 16, it is possible to diametrically reduce the wire-stranded hollow coil body 1 progressively in a stepwise fashion from the hand access portion 8 to the leading distal end 7 in accordance with the lengthwisely divided sections. As an alternative, the wire-stranded hollow coil body 1 may be progressively decreased at its diametrical dimension in a cone-shaped fashion from the hand access portion 8 to the leading distal end 7 as shown at diametrical dimensions DS and D3 in FIG. 17. From this stand of view, "the flexible wire tube being soft at the front end and rigid at the rear end portion" is attained as a requirement for the medical equipment. This realizes a functionally gradient structure which enables the manipulator to feel a smooth shift from the front soft property to the rear rigid property in proportion with a distance from the hand access portion 8.

Even without making the wire-stranded hollow coil body 1 into a cone-shaped or stepwise configuration, a bending rigidity and torque-transmitting capability can be improved to secure a smooth outer surface devoid of undulation between the neighboring coil line elements when compared to the structure in which the outer surface of the coil line elements 2 is not ground. This makes it possible to enhance the performance upon inserting the flexible wire tube into the vascular system and the somatic cavity.

FIG. 18 shows a medical equipment in which the wire-stranded hollow coil body 1 is used as the flexible wire tube. FIGS. 18, 19, 21, 22 and 25 show a flexible endoscope 20 in which the wire-stranded hollow coil body 1 is used as a cloak tube 23. As shown in FIG. 19, the endoscope 20 has four elongated flexible cloak tubes 23 arranged between a front angle manipulator 21 and a rear manipulator 22 in a manner distinguishable from the first reference. Each of the cloak tubes 23 has a manipulator wire 24 surrounded by a flexible outer tube 25.

The flexible endoscope 20 is used to pass the human sigmoidal intenstine when inserted into the colon through the anus and the rectal. By applying the wire-stranded hollow coil body 1 to the endoscope 20, the following advantage specific to the endoscope 20 is obtained.

As opposed to a related art cloak tube 23A constructed from the single-wound coil structure (FIG. 20) so that a helical pitch gap P increases at its outer side of the cloak tube 23A to increase a tensile stress applied to the manipulator wire 24 when passing through the sigmoidal intenstine, it is possible to significantly reduce the tensile stress applied to the manipulator wire 24 because of its high flexibility of the cloak tubes 23 which readily adapt itself to the curved shape configuration in the present invention as shown in FIG. 21.

Figure 22:
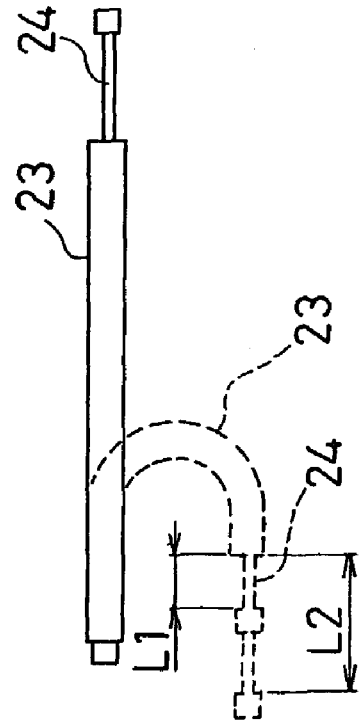
FIG. 22 is another explanatory view of the flexible endscope shown how a cloak tube stretches when subjected to a bending deformation.

As opposed to the related art cloak tube which stretches when passing through the sigmoidal intenstine to significantly increase a length (L2) of the manipulator wire 24 extended from the cloak tube, it is possible to limit the length (L2) to a subject extension length (L1) as shown at broken lines in FIG. 22 since the cloak tubes 23 stretches in significantly small degree even when subjected to the bending deformation.

Figure 23:
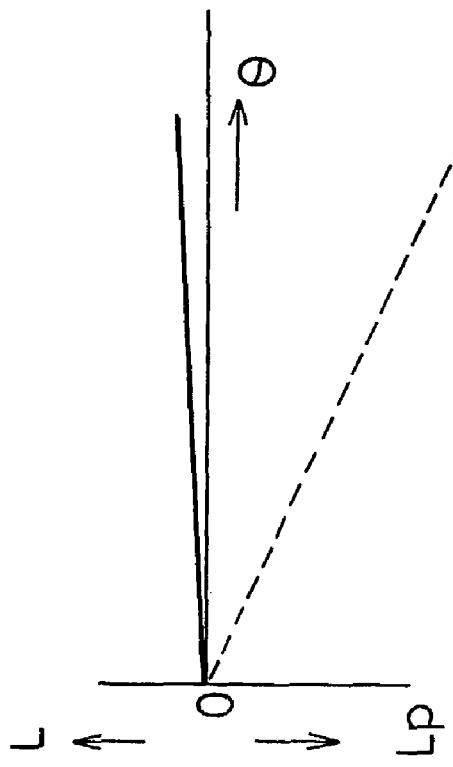
FIG. 23 is a graphical representation showing a relationship between a total bending angle (θ) and an extension length (L)

FIG. 23 shows a relationship between a total bending angle (θ) and an extension length (L) of the manipulator wire 24. It is found from a solid line in FIG. 23 that the flexible linear tube structure makes it possible to render the extension length (L) significantly small as compared to the related art extension length (Lp) (seventh reference) depicted by broken lines.

Figure 25:
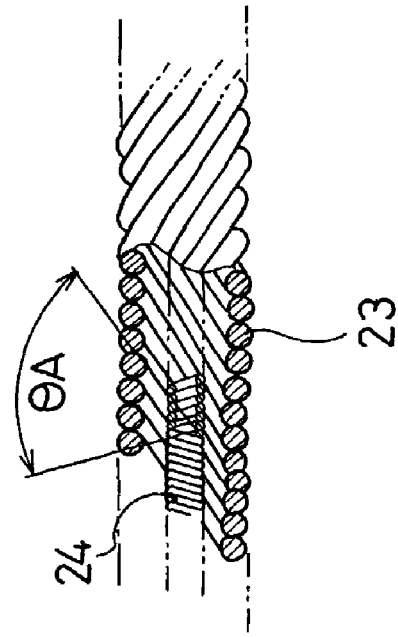
FIG. 25 is a plan view of a cloak tube but partly sectioned.
Figure 24:
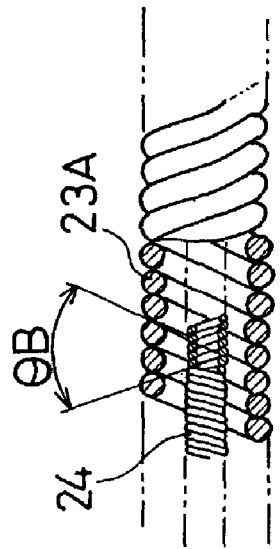
FIG. 24 is a plan view of a related art cloak tube but partly sectioned.

The cloak tube 23 has an increased strand pitch between the coil line elements 2 as compared to a coil pitch of the related art cloak tube 23A as understood by FIGS. 24 and 25. The structure makes it possible to significantly increase a relative friction angle (θA) against the manipulator wire 24 as compared to a relative friction angle (θB) of the related art cloak tube 23A against the manipulator wire 24. This reduces a frictional resistance between the cloak tube 23 and the manipulator wire 24 to greatly improve its push-pull maneuverability. By reversely stranding the cloak tube 23 against the manipulator wire 24 (stranding in an opposite direction), it is possible to determine the relative friction angle (θA) to be around 90 degrees to improve the maneuverability.

The flexible endoscope 20 thus constructed has advantages that enables the leading end to smoothly pass through the sigmoidal intenstine so as to significantly improve a responsiveness and manipulatability of the front angle manipulator 21 actuated by the rear manipulator 22 (FIG. 18).

Figure 26:
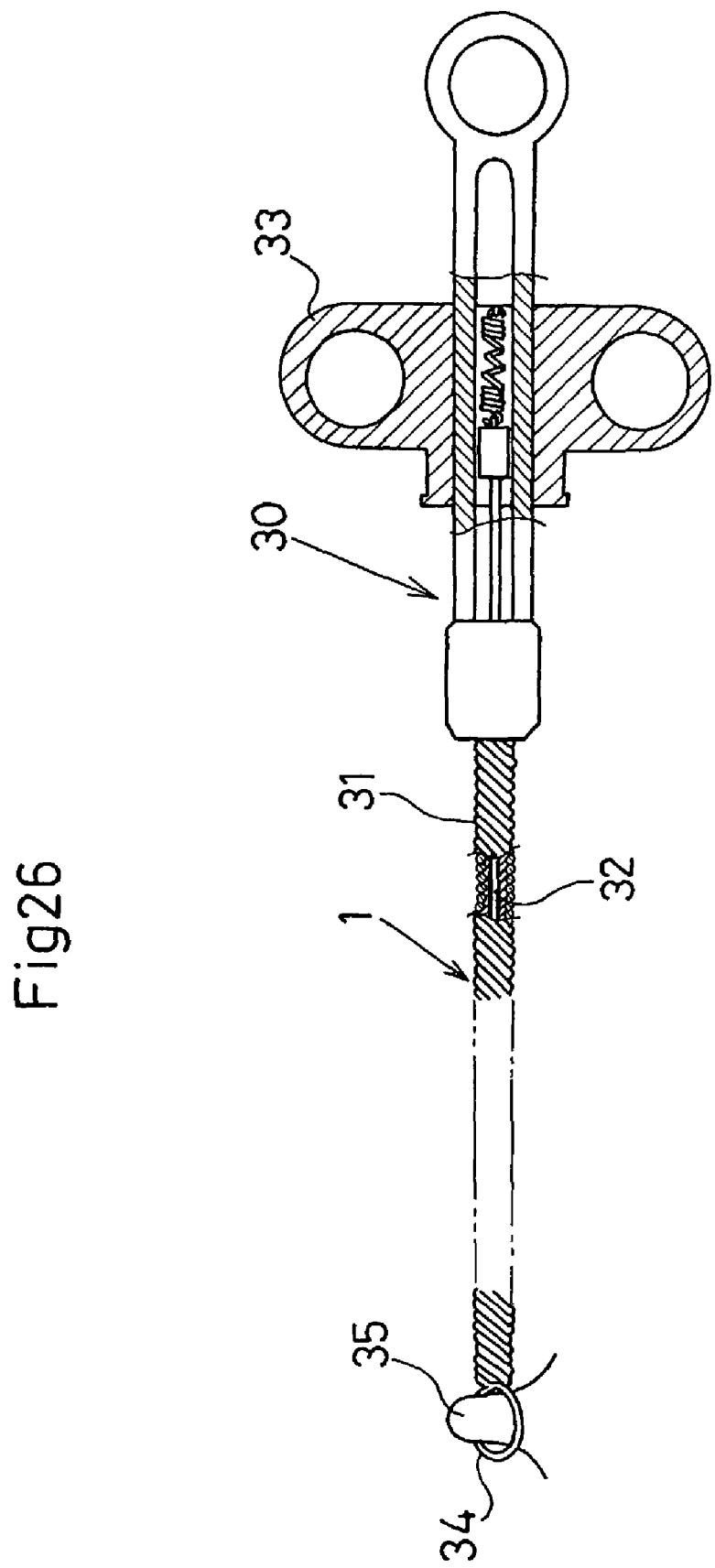
FIG. 26 is a plan view of a endscope treating tool but partly sectioned.

FIG. 26 shows an endoscope treating tool 30 in which a coil sheath 31 is arranged between a rear manipulator 33 and a front detain loop 34. The coil sheath 31 acts as the wire-stranded hollow coil body 1 which has a central hollow area, through which manipulator rope 32 is inserted. In addition to the main advantages, the endoscope treating tool 30 provides the following advantages.

Namely, in the single wound coil sheath disclosed by the eighth reference, the manipulator rope is forcibly stretched so as to deteriorate the manipulatability upon inserting the coil sheath into the somatic cavity, thus loosening a grip of the front detain loop 34 against a polyp 35 so as to disable the front detain loop 34 due to a failure of clutching the polyp 35.

On the contrary, the subject endoscope treating tool 30 has the front detain loop 34 (secured to the coil sheath 31) which stabilizes a grip against the polyp 35 with a good manipulatability so as to overcome the related art drawbacks to significantly improve a curability against the polyp 35.

Figure 27:
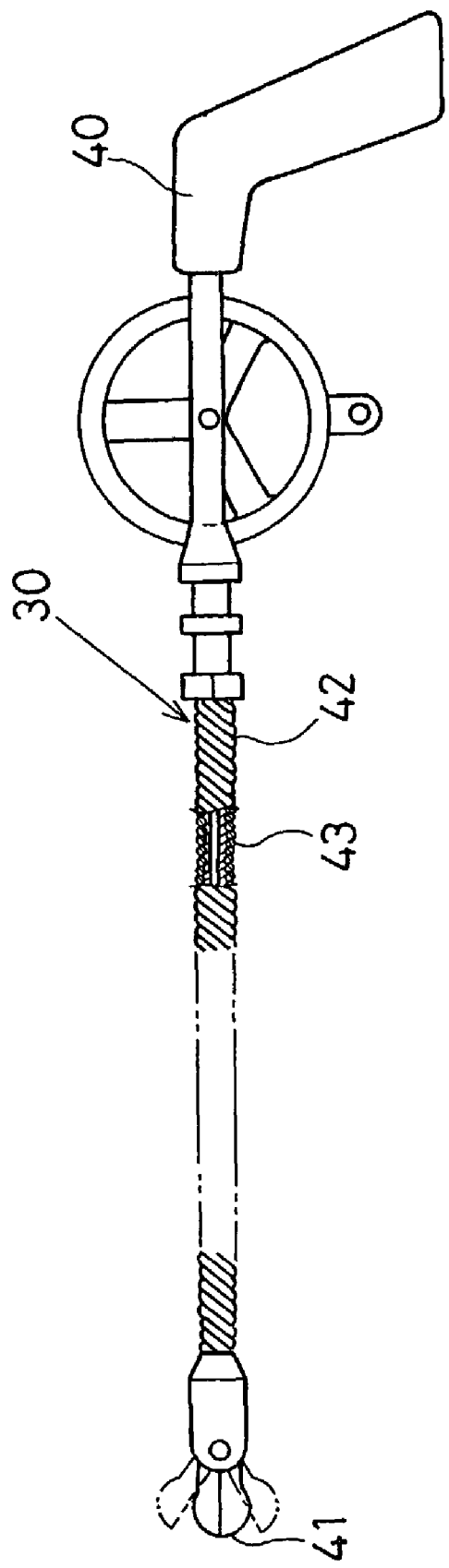
FIG. 27 is a plan view of another endscope treating tool but partly sectioned.

As shown in FIG. 27, the subject endoscope treating tool 30 has a sheath 42 arranged between a front biopsy cup 41 and a rear manipulator 40 in a manner distinguishable from the fifth reference. The sheath 42 serves as the wire-stranded hollow coil body 1 into which a manipulation rope 43 is inserted so as to rotationally move the front biopsy cup 41. The endoscope treating tool 30 into which the wire-stranded hollow coil body 1 is incoporated as the sheath 42, provides the following advantages in addition the main advantages.

Figure 28:
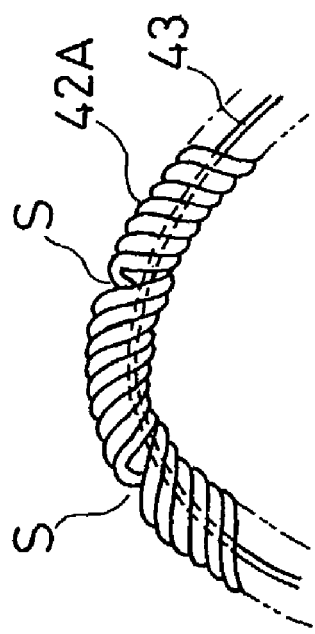
FIG. 28 is a plan view of a related art multi-wound coil sheath.

Namely, therein lies a situation in which an open-and-close actuation of the front biopsy cup 41 is quintessential to precisely clutch the diseased tissue to attain an improved manipulatability and actuation. However, the related art multi-wound coil sheath 42A (FIG. 28) as identified by the fifth reference tends to produce a wider gap S between the neighboring coil line elements when abruptly bended upon inserting into the somatic body. This forcible stretches the manipulation rope 43 to inadvertently twist the front biopsy cup 41 to block its open-and-close action so as to render the open-and-close action unstable.

With the sheath 42 formed by the wire-stranded hollow coil body 1 to effect a high rotation-following capability and high straightness due to the wire-stranded hollow coil configuration, it is possible to prevent the wider gap S from appearing between the neighboring coil line elements when abruptly bended upon inserting into the somatic body. This makes it possible to stabilize the open-close and turn manipulation of the front biopsy cup 41, whereby enabling the manipulator to positively clutch the lesion tissue efficiently with ease.

It is to be noted that since the endoscope treating tool 30 requires a stronger torsional torque when clutching the lesion tissue, the manipulation is further improved by using the structure (FIGS. 13–17) in which the outer surface of the group of the coil line elements 2 is ground. For the same purpose, the structure (FIG. 25) may be used in which the cloak tube 23 and the manipulator wire 24 are reversely stranded each other.

Figure 29:
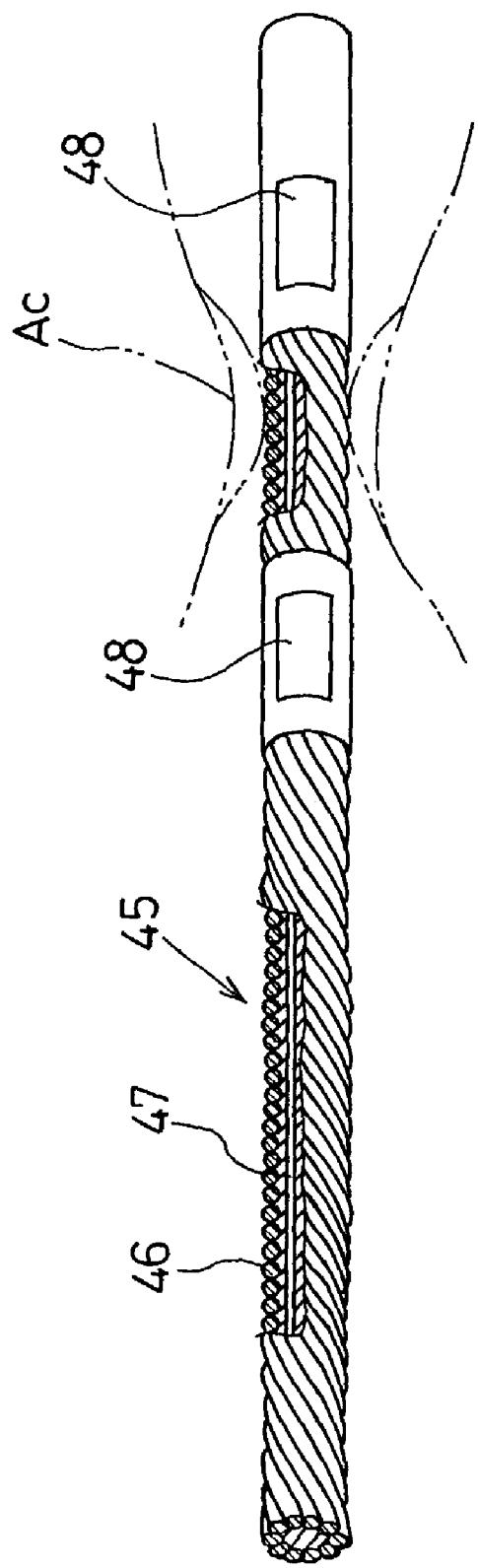
FIG. 29 is a plan view of a pressure sensor type guide wire.
Figure 30:
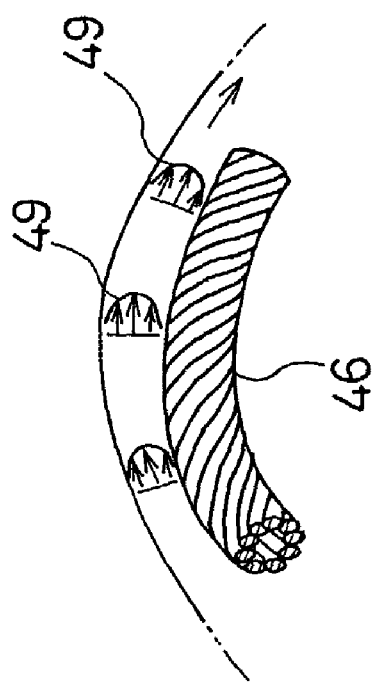
FIG. 30 is an explanatory view of the pressure sensor type guide wire.
Figure 31:
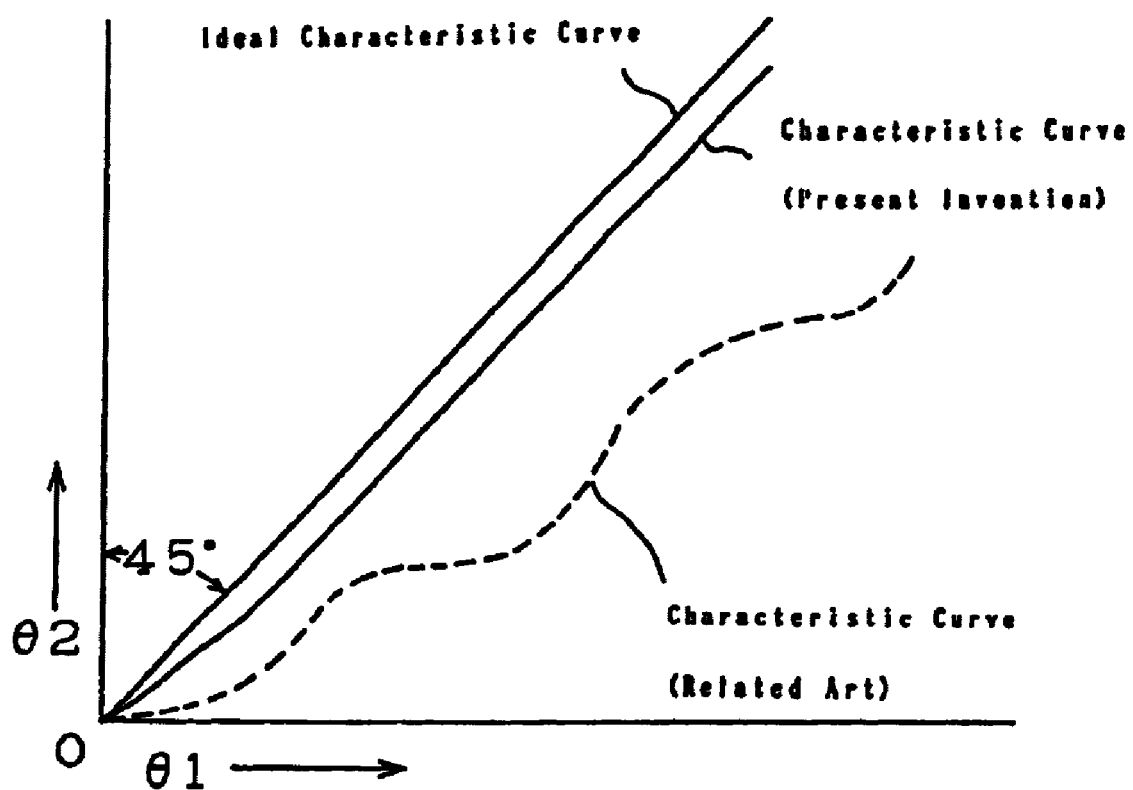
FIG. 31 is a chart illustrating rotational manipulation and twisting characteristics of the related art and the present invention.

FIGS. 29 and 30 show a pressure sensor type guide wire 45 in which a pressure sensor 48 is provided at a front distal end of a flexible hollow tube wire 46 to measure a blood pressure or to monitor a blood pressure wave through a lead line 47 in a manner distinguishable from the sixth reference. With the flexible hollow tube wire 46 into which the wire-stranded hollow coil body 1 is incoporated, the pressure sensor type guide wire 45 provides the following advantages in addition the main advantages.

Namely, with the flexible hollow tube wire prepared by the ordinary hollow coil body, the flexible hollow tube wire is subjected to the bending deformation so that the lead line 47 can be accidentally severed by a tensile force upon inserting it into the tortuous vascular system to confirm a post-operational condition after curing the coronary arterial stenosis (Ac) by way of example. In the case of the single wound flexible hollow tube wire, an excessive wider gap appears between the neighboring coil line elements to produce turbulences in the blood streams near the gap area so as to fluctuate the blood pressure wave measured by the pressure sensor 48 to nullify the measurements.

However, with the flexible hollow tube wire 46 formed by the wire-stranded hollow coil body 1 to effect a high rotation-following capability and high straightness due to the wire-stranded coil configuration, it is possible to prevent the wider gap S from appearing between the neighboring coil line elements when abruptly bended upon inserting into the somatic body. This prevents the turbulences from appearing near the gap S to enable the manipulator to stable measurements by the pressure sensor 48 with a high precision and improved performance.

By applying the structure of FIGS. 13–17 to the flexible hollow tube wire 46 to represent the ground outer surface of the coil line elements, it is possible to define a smooth outer surface of the flexible hollow tube wire 46 to reduce the fluid friction resistance against the blood stream so as to suppress a laminar stream resistance at a boundary layer as shown at a parabolic velocity distribution 49 in FIG. 30. This makes it possible to achieve a necessary amount of the precisely measurable blood stream with a least amount of thrombi deposited on the outer surface of the coil line elements.

With the austenitic stainless steel applied to the wire-stranded hollow coil body 1 and the medical equipment, the description continues with respect to the structure represented by an "austenitic stainless steel" and the "electrolytically polished outer surface of the coil line elements". By way of illustration, the martensitic stainless steel tends to harden with the heat treatment so as to likely stiffen the stranded coil section near the bulge portion 6 under the thermal influence produced at the time of soldering the bulge portion 6, thereby resultantly depriving the stranded coil section of the favorable flexibility. On the other hand, the ferritic stainless steel has the property referred to as "475° C. fragility" and having the property called as "sigma fragility" occurred when heated to approx. 600–800° C. for an extended period of time. Especially, the ferritic stainless steel grows the crystallized particles to reveal "fragility in high temperature" when heated to 950° C. or more, thereby unfavorably deteriorating the quality as a catheter or catheter guide wire due to the thermal influence brought by thermally bonding the bulge portion 6.

However, since the austenitic stainless steel is less subjected to the texture transformation when heated, it is less affected by the heat generated when thermally bonding the bulge portion 6. In addition, the austenitic stainless steel has a relatively small thermal conductivity and a greater coefficient of thermal expansion which is approx. 1.5–1.6 times as great as that of the general stainless steel. This means that the thermal expansion and the thermal stress produced on the wire-stranded hollow coil body 1 by thermally bonding the bulge portion 6 are absorbed by a restricted portion of the wire-stranded hollow coil body 1 near the bulge portion 6. This alleviates the residual stress produced by thermally bonding the bulge portion 6, and thereby providing a good linearity and favorable flexibility with the restricted portion of the wire-stranded hollow coil body 1 near the bulge portion 6.

While the martensitic stainless steel has a quench hardening property by which a tensile strength is augmented, the austenitic stainless steel increases its strength when drawn (work hardening) to be well-suited to the coil line elements of the wire-stranded hollow coil body 1. Since an electric resistance of the austenitic stainless steel is approx, five times as great as that of the carbon steel, and is approx. 1.6 times as great as that of the martensitic stainless steel. This decreases an intensity of the electric current necessary to thermally bond the bulge portion 6, whereby limiting the thermally bonding heat to a necessary minimum so as to lessen a twisting and torsional deformation under the influence of the heat generated by thermally bonding the bulge portion 6.

With the coil line elements 2 specified by the austenitic stainless steel, the coil line elements 2 are magnetized when drawn by a dice tool with an outer surface of the coil line elements 2 mirror-finished. This attracts iron particles on the outer surface of the coil line elements 2 and collects foreign matters between the neighboring coil line elements 2 with the help of the Van del Waals' force based on the intermolecular affinity. When the foreign matters are collected, in addition to a passively-caught rust from an opposed component part, a crevice corrosion occurs between the outer surface of the coil line elements 2 and the foreign matters so as to reduce a corrosion-resistant property. However, with the outer surface of the coil line elements 2 electrolytically polished, oxidized scales are removed to recover an original concentration of chromium component of the coil line elements 2 so as to resultantly improve the corrosion-resistant property.

The wire-stranded hollow coil body 1 is applied not only to the medical equipment but also to a cloak tube into which a flexible wire is inserted. In this instance, any material such as, for example, a general steel wire, a reinforced thin rope or the like can be applied to the coil line elements 2.

As apparent from the foregoing description, the wire-stranded hollow coil body has a flexible hollow wire tube with a high rotation-following capability and a high straightness which provides such good properties as to be appropriately applicable to main constituents of various medical tools to undergo the treatment by inserting it into the vascular system and the somatic cavity. This effectively enhances the quality and the performance of the medical tools so as to contribute to manipulative skill improvements in the medical field. Further, the method of making the wire-stranded hollow coil body enables manufacturers to mass produce high quality medical devices efficiently with a relatively low cost.

What is claimed is:

1. A method of making a wire-stranded hollow coil body comprising a multitude of coil line elements stranded along a predetermined circular line to form a flexible linear metallic tube having a central axial hollow portion, the method comprising steps of:

clamping one end of a primary forming flexible linear metallic tube by means of a rotationally active chuck, and arranging the other end of said primary forming flexible linear metallic tube to be slidable in its lengthwise direction, and clamping said other end by a fixture chuck to impart a tensile force with said primary forming flexible linear metallic tube; and actuating said rotationally active chuck to strand said primary forming flexible linear metallic tube, and concurrently or thereafter heat treating said primary forming flexible linear metallic tube to remove a residual stress upon forming said coil line elements by electrically conducting between said rotationally active chuck, and thereafter withdrawing an elongated core from said primary forming flexible linear metallic tube to provide an axial hollow portion in which said elongated core is placed.

2. A method of making a wire-stranded hollow coil body comprising a multitude of coil line elements stranded along a predetermined circular line to form a flexible linear metallic tube having a central axial hollow portion, the method comprising steps of:

clamping one end of a primary forming flexible linear metallic tube by means of a rotationally active chuck, and clamping mid-portions of said primary forming flexible linear metallic tube by means of mid-clamps, and stranding said primary forming flexible linear metallic tube in different strand turns depending on spans between said rotationally active chuck and each of said mid-clamps, and thereafter withdrawing an elongated core from said primary forming flexible linear metallic tube to provide an axial hollow portion in which said elongated core is placed.

3. A method of making a wire-stranded hollow coil body comprising a multitude of coil line elements stranded along a predetermined circular line to form a flexible linear metallic tube having a central axial hollow portion, the method comprising steps of:

concurrently or after stranding a primary forming flexible linear metallic tube, accommodating lengthwisely divided sections of the primary forming flexible linear metallic tube into heating devices, each of which has a different heating condition depending on said lengthwisely divided sections, so as to heat treat said pluralistically divided sections individually to have residual stresses removed in different degrees, and thereafter withdrawing an elongated core from said primary forming flexible linear metallic tube to provide an axial hollow portion in which said elongated core is placed.

* * * * *